(12) United States Patent
Hupe et al.

(10) Patent No.: US 8,309,769 B2
(45) Date of Patent: Nov. 13, 2012

(54) CRYSTALLINE FORMS OF 2-[2-CHLORO-4-METHYLSULFONY 1-3-(2,2,2-TRIFLUOROETHOXYMETHYL) BENZOYL]CYCLOHEXAN-1,3-DIONE

(75) Inventors: Eike Hupe, Ludwigshafen (DE); Markus Gewehr, Kastellaun (DE); Peter Erk, Frankenthal (DE); Heidi Emilia Saxell, Ludwigshafen (DE); Ulrich Griesser, Axams (AT); Michaela Tischler, Schluesslberg (AT)

(73) Assignee: BASF SE, Ludwigshafen (DE)

( * ) Notice: Subject to any disclaimer, the term of this patent is extended or adjusted under 35 U.S.C. 154(b) by 528 days.

(21) Appl. No.: 12/530,666

(22) PCT Filed: Mar. 14, 2008

(86) PCT No.: PCT/EP2008/053060
§ 371 (c)(1), (2), (4) Date: Sep. 10, 2009

(87) PCT Pub. No.: WO2008/110621
PCT Pub. Date: Sep. 18, 2008

(65) Prior Publication Data
US 2010/0041557 A1  Feb. 18, 2010

(30) Foreign Application Priority Data
Mar. 15, 2007 (EP) .................................. 07104275

(51) Int. Cl.
*C07C 315/00* (2006.01)

(52) U.S. Cl. .......................................................... 568/31
(58) Field of Classification Search ....................... None
See application file for complete search history.

(56) References Cited

U.S. PATENT DOCUMENTS
6,376,429 B1  4/2002  Van Almsick et al.

FOREIGN PATENT DOCUMENTS
CA   2346796 C  *  1/2009
WO   WO 00/21924  4/2000

OTHER PUBLICATIONS

International Search Report completed Jun. 2, 2008, in International Application No. PCT/EP2008/053060, filed Mar. 14, 2008.
International Preliminary Report on Patentability dated Jul. 7, 2009, from corresponding International Application No. PCT/EP2008/053060, filed Mar. 14, 2008.

* cited by examiner

*Primary Examiner* — Porfirio Nazario Gonzalez
*Assistant Examiner* — James Meadows
(74) *Attorney, Agent, or Firm* — Brinks Hofer Gilson & Lione

(57) ABSTRACT

The present invention relates to two crystalline forms of 2-[2-chloro-4-methylsulfonyl-3-(2,2,2-trifluoro-ethoxymethyl) benzoyl]cyclohexan-1,3-dione, which is also known under the common name tembotrione. The invention also relates to a process for the production of these crystalline forms and formulations for plant protection which contain one of these crystalline forms of tembotrione.

18 Claims, 2 Drawing Sheets

CRYSTALLINE FORMS OF 2-[2-CHLORO-4-METHYLSULFONY 1-3-(2,2,2-TRIFLUOROETHOXYMETHYL) BENZOYL]CYCLOHEXAN-1,3-DIONE

This application is a National Stage application of International Application No. PCT/EP2008/053060, filed Mar. 14, 2008, the entire contents of which is hereby incorporated herein by reference. This application also claims the benefit under 35 U.S.C. §119 of European Patent Application No. 07104275.8, filed Mar. 15, 2007, the entire contents of which is hereby incorporated herein by reference.

The present invention relates to two crystalline forms of 2-[2-chloro-4-methylsulfonyl-3-(2,2,2-trifluoro-ethoxymethyl)benzoyl]cyclohexan-1,3-dione, which is also known under the common name tembotrione. The invention also relates to a process for the production of these crystalline forms and formulations for plant protection which contain one of these crystalline forms of tembotrione.

Tembotrione is the herbicidal active substance of the formula I or the tautomers I' and I" and mixtures thereof.

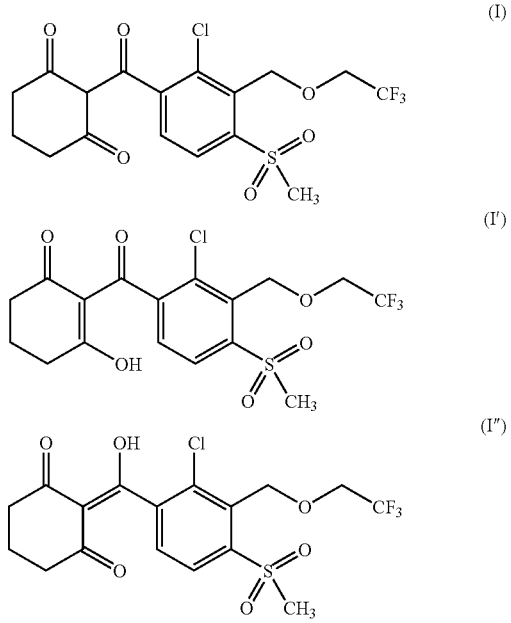

Tembotrione and a general procedure for its production are known from WO 00/21924. This procedure yields tembotrione as an oil or as an amorphous solid. A liquid formulation of tembotrione with isoxadifen was recently introduced onto the market.

For the production of active substances on the industrial scale but also for the formulation of active substances, in many cases knowledge concerning the possible existence of crystalline modifications (also described as crystalline forms) or of solvates of the active substance in question, and knowledge of the specific properties of such modifications and solvates and of methods for their preparation are of decisive importance. A range of active substances can exist in different crystalline but also in amorphous modifications. Polymorphism is the term used in these cases. A polymorph is a solid, crystalline phase of a compound which is characterized by a specific, uniform packing and arrangement of the molecules in the solid.

Different modifications of one and the same active substance can sometimes have different properties, for example differences in the following properties: solubility, vapor pressure, dissolution rate, stability against a phase change into a different modification, stability during grinding, suspension stability, optical and mechanical properties, hygroscopicity, crystal form and size, filterability, density, melting point, stability to decomposition, color and sometimes even chemical reactivity or biological activity.

The applicant's own attempts to convert tembotrione into a crystalline solid by crystallization at first resulted in amorphous products or in complex mixtures of different crystal modifications, which could only be handled with difficulty and whose stability against uncontrolled phase change was unsatisfactory.

It has now surprisingly been found that by suitable processes two previously unknown crystalline, stable modifications of tembotrione which do not display the disadvantages of the amorphous tembotrione are obtained in high purity. These two modifications are also described below as form A and form C.

In addition, the crystal forms A and C according to the invention are easier to handle than the previously known amorphous tembotrione, since during production they are obtained in the form of discrete crystals or crystallites. Compared to mixtures of these forms both the pure form A and also the pure form C display increased stability with regard to conversion into another modification. The stability of formulations which contain tembotrione either in form A or form C is also markedly higher than the stability of formulations which contain mixtures of different modifications of tembotrione. The terms "pure form A" and "pure form C" should be understood to mean that the proportion of the modification in question, based on the total quantity of tembotrione, is at least 90 wt. % and in particular at least 95 wt. %.

Accordingly, a first object of the present invention relates to the crystalline form A of tembotrione. Also an object is a tembotrione which at least 90 wt. % in particular at least 95% consists of the crystalline form A.

The form A according to the invention can be identified by X-ray powder diffractometry on the basis of its diffraction diagram. Thus an X-ray powder diffraction diagram recorded using Cu—Kα radiation (1.54178 Å) at 25° C. shows at least 3, often at least 5, in particular at least 7, and especially all of the reflections quoted in the following table as 2θ values or as interplanar spacings d:

| 2θ | d [Å] |
|---|---|
| 5.5 ± 0.2 | 15.92 ± 0.07 |
| 8.9 ± 0.2 | 9.97 ± 0.07 |
| 11.1 ± 0.2 | 7.93 ± 0.05 |
| 14.0 ± 0.2 | 6.32 ± 0.05 |
| 18.9 ± 0.2 | 4.70 ± 0.04 |
| 23.4 ± 0.2 | 3.79 ± 0.03 |
| 26.7 ± 0.2 | 3.33 ± 0.02 |
| 28.9 ± 0.2 | 3.09 ± 0.02 |
| 36.2 ± 0.2 | 2.48 ± 0.02 |

Studies on single crystals of form A demonstrate that the underlying crystal structure is orthorhombic. The unit cell has the space group Pna2(1). The characteristic data of the crystal structure of form A (determined at −170° C.) are compiled in the following table.

| Crystallographic characteristics of form A | |
|---|---|
| Parameter | Form A |
| class | orthorhombic |
| space group | Pna2(1) |
| a | 31.14(2) Å |
| b | 10.34(1) Å |
| c | 5.52(1) Å |
| α | 90° |
| β | 90° |
| γ | 90° |
| volume | 1778.0(2) Å$^3$ |
| Z | 4 |
| density (calculated) | 1.643 Mg/m$^3$ |
| R$^1$; wR$^2$ | 0.050; 0.101 |
| wavelength | 1.54178 Å | a, b, c = unit cell length
α, β, γ = unit cell angle
Z = number of molecules in the unit cell Form A displays a thermogram with a characteristic melting peak in the range from 110 to 135° C. The melting point, determined as the onset of the melting peak, typically lies in the range from about 118° C. to 124° C., in particular in the range from 119 to 122° C. The values quoted here relate to values determined by differential calorimetry (differential scanning calorimetry: DSC, aluminum closed cup, heating rate 10 K/min).

The production of the form A of tembotrione according to the invention is effected by crystallization from a solution of tembotrione in a suitable organic solvent. Suitable solvents for the crystallization of form A are polar organic solvents which are selected from cyclic ethers such as tetrahydrofuran and dioxan, acetonitrile, methanol, nitromethane, acetic acid, methyl ethyl ketone, pyridine and dimethyl sulfoxide and mixtures thereof.

In order to obtain form A of tembotrione, the crystallization is preferably effected at temperatures of at most 100° C., in particular at most 60° C. and more preferably at most 50° C. Crystallization of form A is preferably effected under controlled conditions, i.e. the conditions of the crystallization are chosen to achieve a slow crystallization rate.

For this, in a first step i) a solution of tembotrione in one of the aforesaid organic solvents is prepared, and then in a second step ii) crystallization of the tembotrione is effected.

The concentration of tembotrione in the solution used for the crystallization naturally depends on the nature of the solvent and the solution temperature and often lies in the range from 100 to 800 g/l. Suitable conditions can be determined by the person skilled in the art by routine experiments.

Preferably the solution used for the crystallization contains tembotrione in a purity of at least 85%, often at least 90%, in particular at least 95%, i.e. the content of organic impurities which are not organic solvents is not more than 15 wt. %, often not more than 10 wt. %, and in particular not more than 5 wt. %, based on the tembotrione present dissolved in the solvent.

The solution used for the crystallization is preferably essentially free from solvents other than those stated. In this context, "essentially free" means that the concentration of other solvents in the tembotrione-containing solution does not exceed 10 wt. %, often 5 wt. %, based on the total quantity of solvent.

The solution of tembotrione can for example be prepared by the following methods:

(1) Dissolution of the tembotrione, preferably in a form different from form A, in one of the aforesaid polar organic solvents, or (2) Preparation of the tembotrione by a chemical reaction and transfer of the reaction mixture, if necessary after removal of reagents and/or side products, into an organic solvent suitable according to the invention.

For the preparation of the solution by dissolution of the tembotrione, essentially any known form of tembotrione can be used. Often amorphous tembotrione or a mixture of different crystalline modifications or a mixture of amorphous and crystalline tembotrione will be used. Also suitable are crystalline forms of tembotrione and mixtures thereof, for example the form C according to the invention described below and the form B also described here, not according to the invention, and mixtures of these forms.

The dissolution of the tembotrione is usually effected at temperatures in the range from 20 to 160° C. In a preferred embodiment of the invention, the dissolution of the tembotrione is effected at elevated temperature, in particular at 50° C. at least, and naturally the temperature used for dissolution will not exceed the boiling point of the solvent. The dissolution is often effected at temperatures in the range from 50 to 140° C. It is, however, preferred to effect crystallisation at temperatures of at most 100° C., in particular at most 60° C. and more preferably at most 50° C.

The solution of the tembotrione can also be prepared by transferring a reaction mixture obtained by a chemical reaction, which contains the tembotrione, if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present, for example water and/or methanol, are removed. The preparation of a solution of the tembotrione by chemical reaction of a suitable precursor of tembotrione can be effected by analogy to the methods which are described in the state of the art cited at the beginning, to which full reference is hereby made.

The crystallization of form A of tembotrione can be effected as follows, for example
- by cooling of the solution which contains the dissolved tembotrione,
- by addition of a solubility-decreasing solvent to the solution which contains the dissolved tembotrione, in particular by addition of a nonpolar organic solvent or by addition of water,
- by concentration of the solution which contains the dissolved tembotrione, or
- by a combination of the aforesaid measures.

The crystallization is as a rule carried out until at least 80 wt. %, preferably at least 90 wt. %, of the tembotrione used crystallizes out.

If the crystallization of form A is effected by cooling, the cooling rate is preferably less than 10 K/min.

The crystallization of form A can be promoted or accelerated by seeding with seed crystals of form A, for example by adding seed crystals of form A before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved tembotrione.

If the crystallization is performed in the presence of seed crystals of form A, these are preferably only added at a temperature at which the saturation concentration of the tembotrione in the solvent in question has been reached, i.e. at or below that temperature at which the dissolved quantity of tembotrione forms a saturated solution in the solvent in question. The person skilled in the art can determine the temperature dependence of the saturation concentration in a solvent in routine experiments.

Alternatively, the crystallization can also be effected by addition of a "non-solvent" (i.e. a solubility decreasing solvent) e.g. by addition of a nonpolar solvent or by addition of water, for example from 5 to 60 vol. %, in particular 20 to 55 vol. % and especially from 30 to 50 vol. %, based on the volume of the polar organic solvent or solvent mixture used for dissolution of the tembotrione. The addition of the nonpolar solvent or the addition of water are preferably effected over a prolonged period, for example over a period from 10 mins to 3 hrs, in particular over a period from 20 mins to 2.5 hrs. If the crystallization of form A is effected by the addition of a "non-solvent", the addition of the non-solvent is preferably at a slow rate, e.g. less than 10% v/v per minute, based on the volume of the tembotrione solution. Often the addition will be done in such a manner that the nonpolar solvent or water is added until the discernable onset of the crystallization and the mixture thus obtained is then left for a time, during which the crystallization of the form A proceeds. If necessary, the mixture can then be cooled for completion of the crystallization.

In particular, the addition of the nonpolar solvent or the addition of water and the addition of seed crystals can be combined.

The addition of the nonpolar solvent can be effected in the form of a pure nonpolar solvent or in the form of a mixture of a nonpolar solvent with a solvent used for the dissolution. Examples of nonpolar solvents are aliphatic and cycloaliphatic hydrocarbons with preferably 5 to 10 C atoms such as pentane, hexane, cyclopentane, cyclohexane, isohexane, heptane, cycloheptane, octane, decane or mixtures thereof.

The isolation of the form A from the crystallization product, i.e. the separation of the form A from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be effected in one or more steps, washing with water often being used in the last washing step. The washing is typically effected at temperatures below 30° C., often below 25° C. and in particular below 20° C., in order to keep the loss of valuable product as small as possible. Next, the form A obtained can be dried and then supplied for further processing. Often, however, the moist active substance obtained after washing, in particular an active substance moist with water, will be supplied directly for the further processing.

By means of the crystallization according to the invention, the form A is obtained with a tembotrione content of as a rule at least 90 wt. %, often 94 wt. %, in particular at least 96 wt. %. The content of form A, based on the total quantity of tembotrione, is typically at least 90% and often at least 95% or at least 96%.

The preparation of the 2-[2-chloro-4-methylsulfonyl-3-(2,2,2-trifluoroethoxy)methylbenzoyl]cyclohexan-1,3-dione used for the production of the form A can be effected by the process described in WO 00/21924, to which full reference is hereby made.

A further object of the present invention relates to the crystalline form C of tembotrione. Also an object is a tembotrione which at least 90 wt. %, in particular at least 95% consists of the crystalline form C.

The form C according to the invention can be identified by X-ray powder diffractometry on the basis of its diffraction diagram. Thus an X-ray powder diffraction diagram recorded using Cu—Kα radiation (1.54178 Å) at 25° C. shows at least 3, often at least 5, and especially all of the reflections quoted in the following table as 2θ values or as interplanar spacings d:

| 2θ | d [Å] |
|---|---|
| 7.4 ± 0.2 | 12.00 ± 0.07 |
| 10.8 ± 0.2 | 8.22 ± 0.05 |
| 14.8 ± 0.2 | 6.00 ± 0.05 |
| 16.6 ± 0.2 | 5.34 ± 0.04 |
| 21.1 ± 0.2 | 4.22 ± 0.03 |
| 21.6 ± 0.2 | 4.11 ± 0.02 |
| 33.6 ± 0.2 | 2.67 ± 0.02 |

Studies on single crystals of form C demonstrate that the underlying crystal structure is monoclinic. The unit cell has the space group P2(1)/n. The characteristic data of the crystal structure of form C (determined at −170° C.) are compiled in the following table.

| Crystallographic characteristics of form C | |
|---|---|
| Parameter | Form C |
| class | monoclinic |
| space group | P2(1)/n |
| a | 15.89(1) Å |
| b | 7.10(1) Å |
| c | 16.14(2) Å |
| α | 90° |
| β | 95.91(1)° |
| γ | 90° |
| volume | 1811.3(4) nm$^3$ |
| Z | 4 |
| density (calculated) | 1.616 Mg/m$^3$ |
| R$^1$; wR$^2$ | 0.053; 0.124 |
| wavelength | 1.54178 Å | a, b, c = unit cell length
α, β, γ = unit cell angle
Z = number of molecules in the unit cell Form C displays a thermogram with a characteristic melting peak in the range from 120 to 132° C. The melting point, determined as the onset of the melting peak, typically lies in the range from about 121° C. to 125° C., in particular in the range from 122 to 125° C. The values quoted here relate to values determined by differential calorimetry (differential scanning calorimetry: DSC, aluminum closed cup, heating rate 10 K/min).

The production of the form C of tembotrione according to the invention is effected by
  crystallization from a hot solution of tembotrione in 2,2-dimethylpropanol (tert. amyl alcohol); or
  crystallization from a hot solution of tembotrione in an aromatic solvent or in a mixture of an aromatic solvent with an aliphatic solvent.

For this, in a first step i) a hot solution of tembotrione in is prepared, and then in a second step ii) crystallization of the tembotrione is effected by rapid cooling.

The term "hot solution" means a solution having a temperature of at least 80° C., in particular at least 90° C. and more preferably at least 100° C.

The concentration of tembotrione in the solution used for the crystallization often lies in the range from 100 to 600 g/l, in particular 250 to 400 g/l.

Preferably the solution used for the crystallization contains tembotrione in a purity of at least 85%, often at least 90%, in particular at least 95%, i.e. the content of organic impurities which are not organic solvents is not more than 15 wt. %, often not more than 10 wt. %, and in particular not more than 5 wt. %, based on the tembotrione present dissolved in the solution.

According to a first embodiment, form C is prepared by crystallization from a hot solution of tembotrione in 2,2-dimethylpropanol (tert. amyl alcohol). The solution used for the crystallization is then preferably essentially free from solvents other than 2,2-dimethyl-propanol. In this context, "essentially free" means that the concentration of solvents including water which are different from 2,2-dimethylpropanol in the tembotrione-containing solution does not exceed 10 wt. % and often 5 wt. %, based on the total quantity of solvent.

According to a second embodiment, form C is prepared by crystallization from a hot solution of tembotrione in an aromatic hydrocarbon solvent or in a mixture of an aromatic hydrocarbon solvent with an aliphatic hydrocarbon solvent. Suitable aromatic hydrocarbon solvents include, e.g., toluene, xylenes, mesitylene, cumene (isopropylbenzene), ethylbenzene, ethyltoluenes, cymenes (isopropyltoluenes) such as m- and p-cymene, and mixtures thereof. Suitable aliphatic hydrocarbon solvents include saturated linear, branched or cyclic hydrocarbons such as n-hexane, n-heptane, n-octane and their branched isomers, cyclopentane, cyclohexane, methylcyclohexane, cylcoheptane and cyclooctane. If a mixture of an aromatic and an aliphatic solvent is used, the volume ratio of aromatic solvent to aliphatic solvent is preferably from 20:80 to 99:1, in particular from 30:70 to 95:5 v/v. The solution used for the crystallization is then preferably essentially free from solvents other than aromatic and aliphatic hydrocarbon solvents. In this context, "essentially free" means that the concentration of solvents including water which are different from hydrocarbon solvents in the tembotrione-containing solution does not exceed 10 wt. % and often 5 wt. %, based on the total quantity of solvent.

For the preparation of the solution, essentially any known form of tembotrione can be used. Often amorphous tembotrione or a mixture of different crystalline modifications or a mixture of amorphous and crystalline tembotrione will be used. Also suitable are crystalline forms of tembotrione and mixtures thereof, for example the form A according to the invention described above and the form B also described here, not according to the invention, and mixtures of these forms.

The dissolution of the tembotrione in 2,2-dimethylpropanol is usually effected at temperatures in the range from 80 to 150° C., in particular in the range from 90 to 130° C., in particular from 100 to 120° C. and often at the boiling point of the respective solvent or solvent mixture used for the crystallization of tembotrione, e.g. at the boiling point of 2,2-dimethylpropanol or at the boiling point of the hydrocarbon solvent or solvent mixture.

The crystallization of form C of tembotrione is effected according to the invention by cooling of the hot solution of tembotrione in the respective solvent. According to a preferred embodiment, cooling is performed rapidly. This is understood to mean that the solution is cooled at a cooling rate of at least 30 K/hr, for example at a cooling rate of 30 to 120 K/hr. Rapid cooling is not necessary, when seed crystals of form C are used.

Preferably, the crystallization is performed in a way that the beginning of the crystallization process occurs at a temperature of at least 80° C., more preferably of temperature of at least 90° C. in particular at least 100° C.

The crystallization is as a rule carried out until at least 60 wt. %, preferably at least 80 wt. %, of the tembotrione used crystallizes out.

The crystallization of form C can be promoted or accelerated by seeding with seed crystals of form C, for example by adding seed crystals of form C before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved tembotrione. If the crystallization is performed in the presence of seed crystals of form C, these are preferably only added at a temperature at which the saturation concentration of the tembotrione in the solvent in question has been reached, i.e. at or below that temperature at which the dissolved quantity of tembotrione forms a saturated solution in the respective solvent (e.g. 2,2-dimethylpropanol or hydrocarbon solvent/solvent mixture). The person skilled in the art can determine the temperature dependence of the saturation concentration in a solvent in routine experiments.

The isolation of the form C from the crystallization product, i.e. the separation of the form C from the mother liquor, is effected by usual techniques such as are described in connection with form A.

By means of the crystallization according to the invention, the form C is obtained with a tembotrione content of as a rule at least 90 wt. %, often at least 94 wt. %, in particular at least 96 wt. %. The content of form C, based on the total quantity of tembotrione, is typically at least 90% and often at least 96%.

In connection with the study on the crystallization of tembotrione, a further modification B was found. Unlike the modifications A and C, modification B cannot be stably formulated.

The form B can be identified by X-ray powder diffractometry on the basis of its diffraction diagram. Thus an X-ray powder diffraction diagram recorded using Cu—Kα radiation (1.54178 Å) at 25° C. shows at least 3, often at least 5, and especially all of the reflections quoted in the following table as $2\theta$ values or as interplanar spacings d:

| $2\theta$ | d [Å] |
| --- | --- |
| 5.6 ± 0.2 | 15.77 ± 0.07 |
| 9.2 ± 0.2 | 9.59 ± 0.07 |
| 11.2 ± 0.2 | 7.87 ± 0.05 |
| 12.7 ± 0.2 | 6.98 ± 0.05 |
| 15.4 ± 0.2 | 5.74 ± 0.03 |
| 18.5 ± 0.2 | 4.79 ± 0.03 |
| 22.6 ± 0.2 | 3.92 ± 0.02 |
| 25.5 ± 0.2 | 3.49 ± 0.02 |

Form B displays a thermogram with a characteristic melting peak in the range from 110 to 130° C. The peak maximum typically lies in the range from 120 to 130° C. The melting point, determined as the onset of the melting peak, typically lies in the range from about 118° C. to 123° C., in particular in the range 119 to 122° C. The values quoted here relate to values determined by differential calorimetry (differential scanning calorimetry: DSC, aluminum closed cup, heating rate 10 K/min).

The production of the modification B is effected analogously to the production of the modification A, using n-pentanol instead of 2,2-dimethylpropanol as the solvent.

The following illustrations and examples serve to illustrate the invention and should not be regarded as limiting.

FIG. 1 shows an X-ray powder diffraction diagram of form A. The X-ray diffraction diagram of form A was recorded with a Bruker-AXS Co. D-5000 diffractometer in reflection geometry in the range from $2\theta=2°-40°$ with a step width of $0.02°$ using Cu—K$\alpha$ radiation (1.54178 Å) at 25° C.

Figure 1:
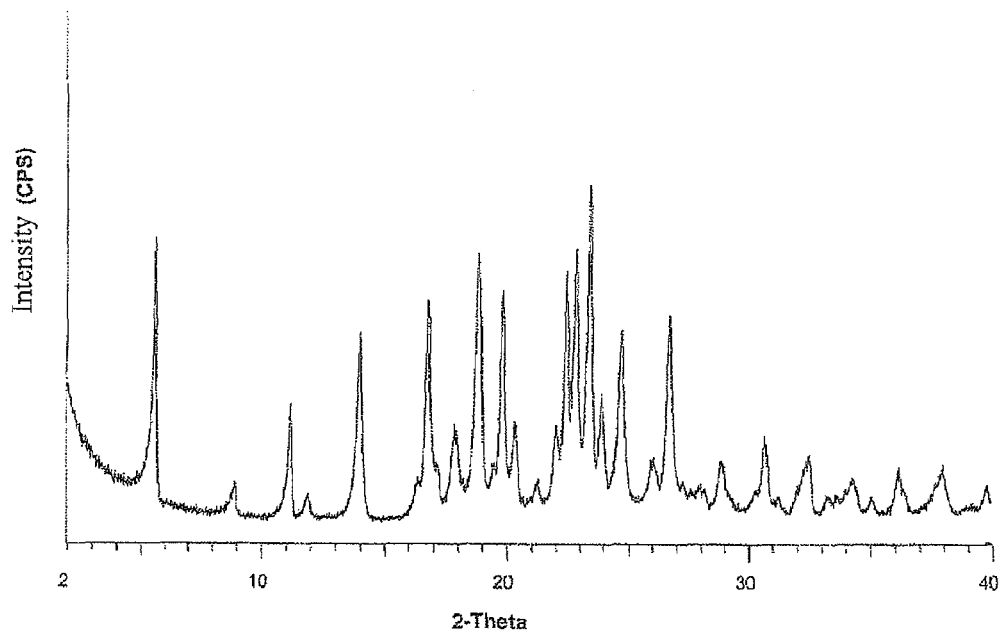
Figure 2:
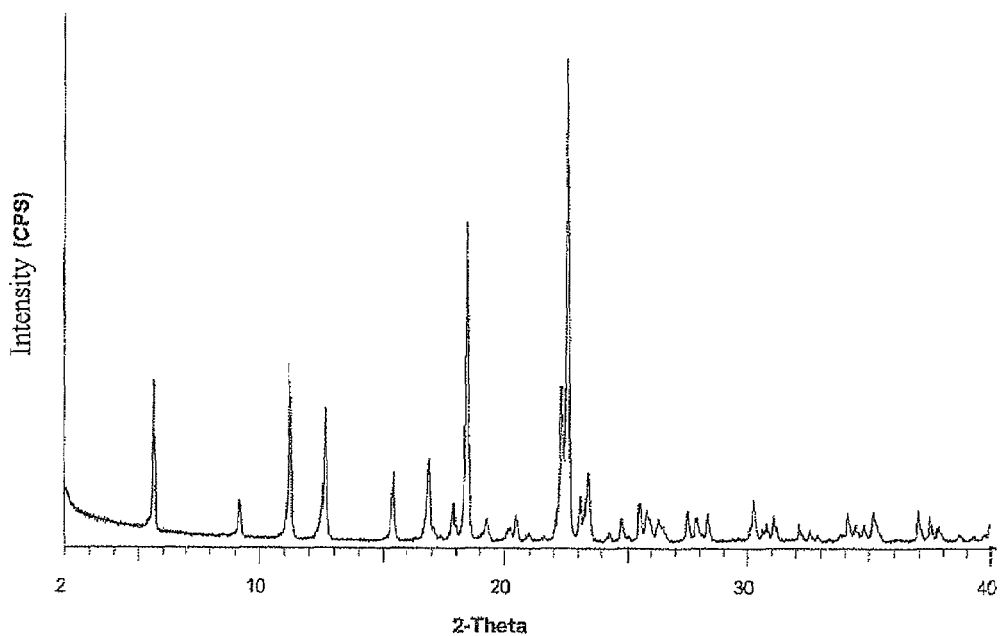
FIG. 2 shows an X-ray powder diffraction diagram of form B. The X-ray diffraction diagram was recorded under the conditions stated for FIG. 1.
Figure 3:
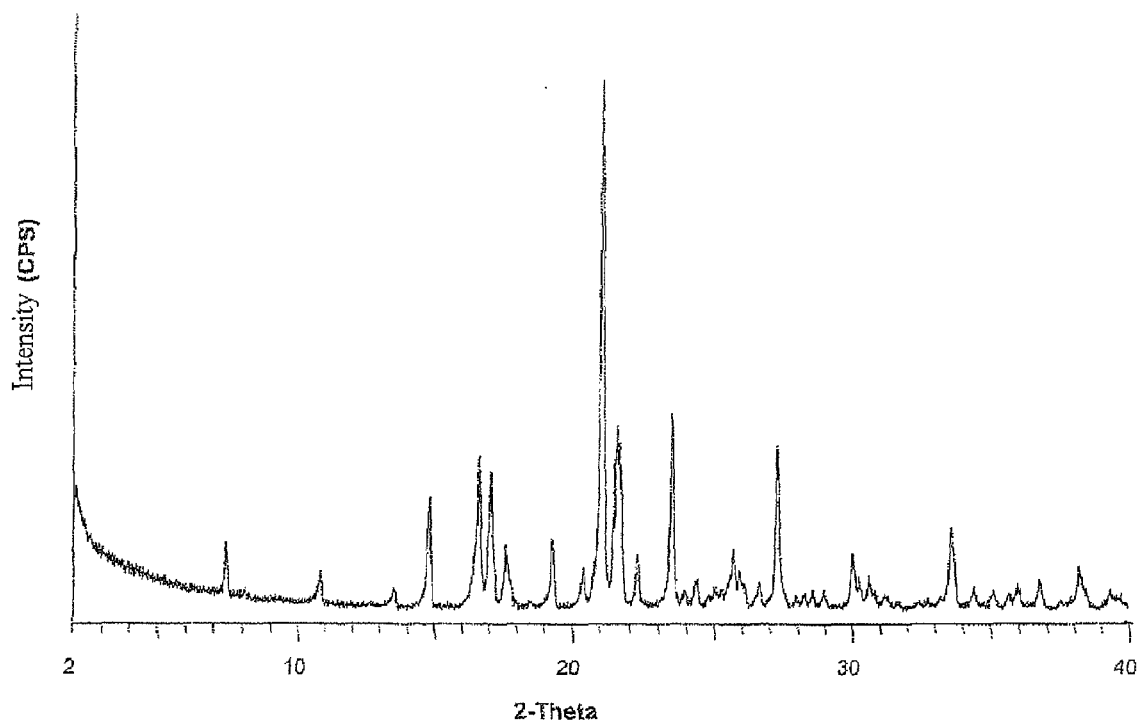
FIG. 3 shows an X-ray powder diffraction diagram of form C. The X-ray diffraction diagram was recorded under the conditions stated for FIG. 1.

The melting points were determined using DSC with a Mettler Co. Mettler Toledo DSC 25 with a heating rate of 10 K/min in the range from 25° to +140° C. The sample weight was 5 to 10 mg.

Single crystal X-ray diffraction. X-ray diffraction data was collected at 103(2) K on a Bruker AXS CCD Detector, using graphite-monochromated CuK$\alpha$ radiation ($\lambda$=1.54178 Å). The structure was solved with direct methods, refined, and expanded by using Fourier techniques with the SHELX-97 software package.

Preparation of Form A of Tembotrione by Crystallization from an Organic Solvent with Cooling Example 1

150 mg of tembotrione were dissolved in 0.15 ml of boiling methanol in a test vessel. The test vessel was sealed and placed in an ice-water bath and left there for about 40 mins. In this manner, tembotrione was obtained in the form of crystalline prisms, which were isolated and analyzed by X-ray powder diffractometry (XRD). On the basis of the characteristic reflections, form A was identified.

Examples 2-9

A saturated solution of about 50 mg of tembotrione in the solvents stated in Table 1 was prepared in a test vessel at the boiling point of the solvent. The test vessel was sealed and placed in an ice-water bath and left there for about 40 mins. In this manner, tembotrione was obtained in the form of crystals, which were isolated and analyzed by X-ray powder diffractometry (XRD). On the basis of the characteristic reflections, form A was identified.

TABLE 1

| Example | Solvent | Crystal form |
| --- | --- | --- |
| 2 | acetic acid | small prisms, needles |
| 3 | acetonitrile | prisms |
| 4 | dioxan | needles and prisms |
| 5 | tetrahydrofuran | small prisms |
| 6 | ethyl methyl ketone | prisms |
| 7 | pyridine | prisms |
| 8 | dimethyl sulfoxide | small prisms, needles |
| 9 | nitromethane | prisms |

Preparation of Form A of Tembotrione by Crystallization from an Organic Solvent by Addition of a $2^{nd}$ Solvent Examples 10 TO 13

A saturated solution of about 50 mg of tembotrione in the $1^{st}$ solvent stated in Table 2 was prepared at room temperature in a test vessel. Next the $2^{nd}$ solvent was added dropwise until the onset of crystallization. The test vessel was sealed and left at room temperature for 16 hrs. In this manner, tembotrione was obtained in the form of crystals, which were isolated and analyzed by X-ray powder diffractometry (XRD). On the basis of the characteristic reflections, form A was identified.

TABLE 2

| Example | $1^{st}$ Solvent | $2^{nd}$ Solvent | Crystal form |
| --- | --- | --- | --- |
| 10 | pyridine | n-heptane | prisms |
| 11 | dioxan | n-heptane | needles and prisms |
| 12 | acetonitrile | $H_2O$ | prisms, needles |
| 13 | dioxan | $H_2O$ | prisms |

Preparation of Form C of Tembotrione by Crystallization from 2,2-Dimethylpropanol Example 14

150 mg of tembotrione were dissolved in 0.50 ml of boiling 2,2-dimethylpropanol in a test vessel. The test vessel was sealed and placed in an ice-water bath and left there for about 40 mins. In this manner, tembotrione was obtained in the form of crystalline prisms, which were isolated and analyzed by X-ray powder diffractometry (XRD). On the basis of the characteristic reflections, form C was identified.

Preparation of Form C of Tembotrione by Crystallization from a Mixture of Toluene and N-Octane Example 15

In a round bottom flask, 7.6 g of tembotrione were dissolved at 110° C. in 20 ml of toluene and the obtained solution was filtered at 110° C. Then 20 ml of n-octane were added and the mixture was stirred at 110° C. until a clear solution was obtained. The solution was cooled on an oil bath to 101° C. and then some seed crystals of the form C (tip of a spatula) were added without stirring. The turbid solution was cooled to room temperature and then stored over night at 6° C. A solid precipitate was filtered off and dried on filter paper. In this manner, tembotrione was obtained in the form of crystalline material, which was analyzed by X-ray powder diffractometry (XRD). On the basis of the characteristic reflections, form C was identified.

Preparation of Form B of Tembotrione by Crystallization from n-Pentanol (not According to Invention)

Comparative Example 1

150 mg of tembotrione were dissolved in 0.20 ml of boiling n-pentanol in a test vessel. The test vessel was sealed and placed in an ice-water bath and left there for about 40 mins. In this manner, tembotrione was obtained in the form of crystalline prisms, which were isolated and analyzed by X-ray powder diffractometry (XRD). On the basis of the characteristic reflections, form B was identified.

Comparative Example 2

Analogously to Comparative Example 1, a saturated solution of tembotrione in boiling ethyl acetate was prepared and cooled. In this manner, tembotrione was obtained in the form of crystalline prisms and platelets, which were isolated and analyzed by X-ray powder diffractometry (XRD). On the basis of the characteristic reflections, form B was identified.

Comparative Experiments on the Crystallization of Tembotrione

Comparative Examples 3-10

A saturated solution of about 50 mg of tembotrione in the solvents stated in Table 3 was prepared in a test vessel at the boiling point of the solvent. The test vessel was sealed and placed in an ice-water bath and left there for about 40 mins. In this manner, tembotrione was obtained in the form of crystals, which were isolated and analyzed by X-ray powder diffractometry (XRD). In all cases, mixtures of different modifications were obtained.

TABLE 3

| Comp. Ex. | Solvent | Crystal form | Modification |
| --- | --- | --- | --- |
| 3 | ethanol | prisms | A + B |
| 4 | 1-propanol | prisms, needles | A + B |
| 5 | 1-butanol | prisms | B + C |
| 6 | 2-propanol | needles, agglomerates | A + B |
| 7 | 1-hexanol | prisms | B + C |
| 8 | tetrachloromethane | agglomerates, prisms | B + C |
| 9 | toluene | agglomerates, prisms | B + C |
| 10 | xylene | agglomerates, prisms | B + C |

Comparative Examples 11-20

A saturated solution of about 50 mg of tembotrione in the solvents stated in Table 4 was prepared in a test vessel at the boiling point of the solvent. The test vessel was sealed and placed in polystyrene container and left there overnight. In this manner, tembotrione was obtained in the form of crystals, which were isolated and analyzed by X-ray powder diffractometry (XRD). In all cases, mixtures of different modifications were obtained.

TABLE 4

| Comp. Ex. | Solvent | Crystal form | Modification |
| --- | --- | --- | --- |
| 11 | ethanol | prisms, agglomerates | A + B |
| 12 | 1-propanol | prisms, needles | A + B |
| 13 | 1-butanol | prisms | B + C |
| 14 | 2-propanol | small prisms | A + B |
| 15 | n-pentanol | prisms | B + C |
| 16 | 2,2-dimethylpropanol | small agglomerates | B + C |
| 17 | 1-hexanol | small prisms, agglomerates | B + C |
| 18 | tetrachloromethane | agglomerates, prisms | B + C |
| 19 | toluene | agglomerates | B + C |
| 20 | xylene | agglomerates, prisms | B + C |

Comparative Examples 21 to 22

A saturated solution of about 50 mg of tembotrione in the 1st solvent stated in Table 5 was prepared at room temperature in a test vessel. Next hexane or water as the $2^{nd}$ solvent was added dropwise until the onset of crystallization. The test vessel was sealed and left at room temperature for 16 hrs. In this manner, tembotrione was obtained in the form of crystals, which were isolated and analyzed by X-ray powder diffractometry (XRD). In all cases mixtures of modifications A and B were obtained.

TABLE 5

| Comp. Ex. | $1^{st}$ Solvent | $2^{nd}$ Solvent | Crystal form | Modification |
| --- | --- | --- | --- | --- |
| 21 | acetone | water | needles | A + B |
| 22 | trichloromethane | n-hexane | prisms | A + B |
| 23 | dichloromethane | n-hexane | needles & prisms | A + B |

Studies on the Stability of the Modifications of Tembotrione

The form in question or mixtures of different forms of tembotrione were suspended in a mixture of methanol with water (volume ratio methanol:water 1:9) at temperatures in the range from 10 to 30° C., and the temperature varied cyclically at a rate of 0.33 K min$^{-1}$.

After 2 days under these conditions, a mixture of forms A, B and C had converted into form A.

After 8 days under these conditions, the pure modifications A and C were unchanged.

After 3 days, modification B had converted completely into modification C.

Just like the known amorphous tembotrione, the forms A and C of tembotrione are suitable as herbicides, however it is superior to this as regards its handling and formulation properties. The invention thus also relates to plant protection agents containing the crystalline forms A or C and additives usual for the formulation of plant protection agents, in particular plant protection agents in the form of aqueous suspension concentrates (so-called SC's) or non-aqueous suspension concentrates (so-called OD's), and plant protection agents in the form of powders (so-called WP's) and granules (so-called WG's) dispersible in water. The invention also relates to a process for combating undesired plant growth, which is characterized in that the form A or C of tembotrione, preferably as a suitable active substance preparation, is used on plants, their habitat and/or on seeds.

The plant protection agents which contain tembotrione in the form A or C combat plant growth, in particular monocotyledonous weed species such as *Avena, Lolium, Alopecurus, Phalaris, Echinochloa, Digitaria, Setaria, Cyperus* species, *Agropyron, Cynodon, Imparato* and *Sorghum*, and dicotyledonous weed species such as *Galium, Viola, Veronica, Lamium, Stellaria, Amaranthus, Sinapsis, Ipomoea, Matricaria, Abutilon, Sida, Convolvulus, Cirsium, Rumex* and *Artemisia* on non-cultivated areas very well, particularly at high application levels. In crops such as wheat, barley, rye, rice, maize, sugar beet, soya and cotton, they are active against weeds and noxious grasses, without harming the crop plants significantly. This effect occurs above all at low application levels.

Depending on the particular application method, the forms A and C of tembotrione or the plant protection agents containing them can also be used in a further number of crop plants for the elimination of undesired plants. Possible crops for example include the following:

*Allium cepa, Ananas comosus, Arachis hypogaea, Asparagus officinalis, Avena sativa, Beta vulgaris* spec. *altissima,*

*Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragara vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus armeniaca, Prunus avium, Prunus cerasus, Prunus dulcis, Prunus domestica, Prunus persica, Pyrus communis, Ribes sylvestre, Ricinus communis, Saccharum officinarum, Secale cereale, Sinapis alba, Solanum tuberosum, Sorghum bicolor* (*S. vulgare*), *Theobroma cacao, Trifolium pratense, Triticale, Triticum aestivum, Triticum durum, Vicia faba, Vitis vinifera* and *Zea mays.*

In addition, tembotrione in the form A or C or the plant protection agents containing them can also be used in crops which through breeding including genetic engineering methods are tolerant towards the action of herbicides.

Further, tembotrione in the form A or C or the plant protection agents containing them can also be used in crops which through breeding including genetic engineering methods are tolerant towards insect or fungal attack.

The forms A and C of tembotrione are also just as suitable as the known amorphous tembotrione for the defoliation and desiccation of plant parts, for example for crop plants such as cotton, potato, rape, sunflower, soya bean or field beans, in particular cotton. In this regard, embodiments of the invention also relate to agents for the desiccation and/or defoliation of plants, processes for the production of these agents and methods for the desiccation and/or defoliation of plants using the forms A and C of tembotrione.

The forms A and C of tembotrione are in particular suitable as desiccants for the desiccation of the aboveground parts of crop plants such as potato, rape, sunflower and soya bean, but also cereals. This enables completely mechanical harvesting of these important crop plants.

Also of scientific interest is the facilitation of harvesting which is enabled by the time-concentrated dropping or reduction of the strength of attachment to the tree with citrus fruits, olives or other species and varieties of pomaceous, stone and shelled fruit. The same mechanism, i.e. the promotion of the formation of separation tissue between fruit or leaf and shoot of the plants is also significant for well-controlled defoliation of useful plants, in particular cotton.

In addition, the shortening of the time interval in which the individual cotton plants become ripe leads to heightened fiber quality after the harvest.

Tembotrione in the forms A or C or the plant protection agents containing them can for example be used in the form of directly sprayable aqueous solutions, powders, suspensions and also high concentration aqueous, oily or other suspensions, oil suspensions, pastes, dusting agents, scattering agents or granules by spraying, misting, dusting, scattering or pouring. The use forms are determined by the use purposes; in each case, they should ensure the finest possible distribution of the active substances according to the invention.

The plant protection agents according to the invention contain tembotrione either in form A or in form C, i.e. in a purity, based on the modification in question, of at least 90 wt. %, and additives and/or carriers such as are usual for the formulation of plant protection agents. In such plant protection agents, the quantity of active substance, i.e. the total quantity of tembotrione and of other active substances if necessary, normally lies in the range from 1 to 98 wt. %, in particular in the range from 10 to 95 wt. %, based on the total weight of the plant protection agent.

All solid and liquid substances which are normally used as carriers in plant protection agents, in particular in herbicide formulations are possible as carriers.

Solid carriers are for example mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder and other solid carriers.

Liquid carriers, as well as water, are also organic liquids, for example mineral oil fractions of medium to high boiling point such as kerosene and diesel oil, also coal tar oils and oils of plant or animal origin, aliphatic, cyclic and aromatic hydrocarbons, for example paraffins, tetrahydronaphthalene, alkylated naphthalenes and derivatives thereof, alkylated benzenes and derivatives thereof, including aromatic and non-aromatic hydrocarbon mixtures, for example the products marketed under the trade names Exxsol and Solvesso, alcohols such as propanol, butanol and cyclohexanol, ketones such as cyclohexanone, and strongly polar solvents, for example amides such as N-methyl-pyrrolidone.

Typical additives include surface-active substances, in particular those wetting agents, emulsifiers and dispersant (additives) normally used in plant protection agents, and also viscosity-modifying additives (thickeners and rheology modifiers), antifoaming agents, antifreeze agents, pH adjusting agents, stabilizers, anticaking agents and biocides (preservatives).

Possible surface-active substances are preferably anionic and nonionic surfactants. Protective colloids are also suitable surface-active substances.

The quantity of surface-active substances will as a rule be 0.1 to 50 wt. %, in particular 0.5 to 30 wt. %, based on the total weight of the plant protection agents according to the invention, or 0.5 to 100 wt. %, based on the total quantity of solid active substances in the formulation. Preferably, the surface-active substance include at least one anionic surface-active substance and at least one nonionic surface-active substance, and the proportion of anionic to nonionic surface-active substance typically lies in the range from 10:1 to 1:10.

Examples of anionic surfactants include alkyl aryl-sulfonates, aromatic sulfonates, for example ligninsulfonates (Borresperse types, Borregaard), phenylsulfonates, naphthalenesulfonates (Morwet types, Akzo Nobel), dibutylnaphthalenesulfonates (Nekal types, BASF), alkyl sulfates, in particular fatty alcohol sulfates, lauryl sulfates, and sulfated hexadeca-; heptadeca- and octadecanols, alkylsulfonates, alkyl ether sulfates, in particular fatty alcohol (poly)glycol ether sulfates, alkyl aryl ether sulfates, alkyl polyglycol ether phosphates, polyarylphenyl ether phosphates, alkyl-sulfosuccinates, olefin sulfonates, paraffin sulfon-ates, petroleum sulfonates, taurides, sarcosides, fatty acids, alkylnaphthalenesulfonic acids, naphthalene-sulfonic acids, ligninsulfonic acids, condensation products of sulfonated naphthalenes with formaldehyde, condensation products of sulfonated naphthalenes with formaldehyde and phenol and optionally urea and condensation products of phenolsulfonic acid with formaldehyde and urea, lignin sulfite waste liquor, alkyl phosphates, alkyl aryl phosphates, for example tristyryl phosphates, and polycarboxylates such as for example polyacrylates, maleic anhydride/olefin copolymers (for example Sokalan® CP9, BASF), including the alkali metal, alkaline earth, ammonium and amine salts of the aforesaid substances. Preferred anionic surface-active substances are those which bear at least one sulfonate group and in particular the alkali metal and ammonium salts thereof.

Examples of non-ionic surface-active substances are alkylphenol alkoxylates, in particular ethoxylates and ethoxylate-copropoxylates of octylphenol, isooctylphenol, nonylphenol and tributylphenol, di- and tristyrylphenol alkoxylates, alcohol alkoxylates, in particular fatty alcohol ethoxylates and fatty alcohol ethoxylate-copropoxylates, for example alkoxylated isotridecanol, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, ethoxylated fatty acid amides, ethoxylated fatty acid esters, alkyl polyglycosides, ethoxylated alkyl polyglycosides, sorbitan fatty acid esters, ethoxylated sorbitan fatty acid esters, glycerol fatty acid esters, lower molecular weight polyalkylene oxides such as polyethylene glycol, polypropylene oxide, polyethylene oxide co-propylene oxide di- and tri-block copolymers, and mixtures thereof. Preferred nonionic surface-active substances are fatty alcohol ethoxylates, alkyl polyglycosides, glycerol fatty acid esters, castor oil ethoxylates, fatty acid ethoxylates, fatty acid amide ethoxylates, lanolin ethoxylates, fatty acid polyglycol esters, ethylene oxide propylene oxide block copolymers and mixtures thereof.

Protective colloids are typically water-soluble, amphiphilic polymers which unlike the aforesaid surfactants typically have molecular weights over 2,000 daltons (number average). Examples thereof are proteins and denatured proteins such as casein, polysaccharides such as water-soluble starch derivatives and cellulose derivatives, hydrophobically modified starches and celluloses, for example methylcellulose, and also polycarboxylates such as polyacrylic acid, acrylic acid copolymers and maleic acid copolymers (BASF Sokalan types), polyvinyl alcohol (Mowiol types from Clariant), polyalkoxylates, polyvinylpyrrolidone, vinylpyrrolidone copolymers, polyvinyl amines, polyethyleneimines (Lupasol types from BASF) and higher molecular weight polyalkylene oxides such as polyethylene glycol, polypropylene oxides, and polyethylene oxide co-polypropylene oxide di- and tri-block copolymers.

The plant protection agents according to the invention can also contain one or more additives modifying the viscosity (rheology modifiers). These are understood in particular to mean substances and substance mixtures which impart modified flow behavior to the formulation, for example a high viscosity in the resting state and low viscosity in the moving state. The nature of the rheology modifier is determined by the nature of the formulation. As examples of rheology modifiers, inorganic substances, for example layer silicates and organically modified layer silicates such as bentonites or attapulgites (for example Attaclay®, Engelhardt Co.), and organic substances such as polysaccharides and heteropolysaccharides such as Xanthan Gum® (Kelzan® from Kelco Co.), Rhodopol® 23 (Rhone Poulenc) or Veegum® (R.T. Vanderbilt Co.) should be mentioned. The quantity of the viscosity-modifying additives is often 0.1 to 5 wt. %, based on the total weight of the plant protection agent.

Examples of antifoaming agents are the silicone emulsions known for this purpose (Silikon® SRE, Wacker Co. or Rhodorsil® from Rhodia Co.), long-chain alcohols, fatty acids and salts thereof, foam suppressants of the aqueous wax dispersion type, solid foam suppressants (so-called Compounds) and organofluorine compounds and mixtures thereof. The quantity of antifoaming agent is typically 0.1 to 1 wt. %, based on the total weight of the plant protection agent.

The plant protection agents according to the invention can also contain preservatives for stabilization. Suitable preservatives are those based on isothiazol-ones, for example Proxel® from ICI Co., or Acticide® from Thor Chemie Co. or Kathon® MK from Rohm & Hass Co. The quantity of preservative is typically 0.05 to 0.5 wt. %, based on the total weight of the SC.

Aqueous plant protection agents, i.e. those with an aqueous carrier, often contain antifreeze agents. Suitable antifreeze agents are liquid polyols, for example ethylene glycol, propylene glycol or glycerine, and urea. The quantity of antifreeze agent is as a rule 1 to 20 wt. %, in particular 5 to 10 wt. %, based on the total weight of the aqueous plant protection agent.

If the plant protection agents containing the crystalline modification A or C are used for seed treatment, they can also contain normal components such as are used for seed treatment, for example in dressing or coating. In addition to the aforesaid components, these include in particular colorants, adhesives, fillers and plasticizers.

All the dyes and pigments usual for such purposes are possible as colorants. Both pigments of low solubility in water and also dyes soluble in water are usable here. As examples, the dyes and pigments known under the names Rhodamin B, C.I. Pigment Red 112 and C.I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 10 and Basic Red 108 may be mentioned. The quantity of colorant will normally not constitute more than 20 wt. % of the formulation and preferably lies in the range from 0.1 to 15 wt. %, based on the total weight of the formulation.

All binders normally usable in dressings come under consideration as adhesives. Examples of suitable binders include thermoplastic polymers such as poly-vinylpyrrolidone, polyvinyl acetate, polyvinyl alcohol and tylose and also polyacrylates, polymethacrylates, polybutenes, polyisobutenes, polystyrene, polyethylene amines, polyethylene amides, the aforesaid protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropyl cellulose and starch derivatives and modified starches, dextrins, maltodextrins, alginates and chitosans, and also fats, oils, proteins, including casein, gelatin and zein, gum Arabic and shellac. The adhesives are preferably plant-compatible, i.e. they exhibit no, or no significant, phytotoxic effects. The adhesives are preferably biodegradable. The adhesive is preferably selected such that it acts as a matrix for the active components of the formulation. The quantity of adhesive will normally not constitute more than 40 wt. % of the formulation and preferably lies in the range from 1 to 40 wt. % and in particular in the range from 5 to 30 wt. %, based on the total weight of the formulation.

In addition to the adhesive, the formulation for seed treatment can also contain inert fillers. Examples of these are the aforesaid solid carriers, in particular finely divided inorganic materials such as clays, chalk, bentonite, kaolin, talc, perlite, mica, silica gel, diatomaceous earth, quartz powder and montmorillonite but also fine-particle organic materials such as wood flour, cereal flour, active charcoal and the like. The quantity of filler is preferably selected such that the total quantity of filler does not exceed 70 wt. %, based on the total weight of all non-volatile components of the formulation. Often, the quantity of filler lies in the range from 1 to 50 wt. %, based on the total weight of all non-volatile components of the formulation.

In addition, the formulation for seed treatment can also contain a plasticizer which increases the flexibility of the coating. Examples of plasticizers are oligomeric polyalkylene glycols, glycerine, dialkyl phthalates, alkylbenzyl phthalates, glycol benzoates and comparable compounds. The quantity of plasticizer in the coating often lies in the range from 0.1 to 20 wt. %, based on the total weight of all non-volatile components of the formulation.

A preferred embodiment of the invention relates to liquid formulations of the forms A or C. In addition to the solid active substance phase, these have at least one liquid phase, in which tembotrione is present in form A or C in the form of dispersed fine particles. Possible liquid phases are essentially water and those organic solvents in which the form A or form C is only slightly soluble, or insoluble, for example those wherein the solubility of the form A or form C at 25° C. and 1013 mbar is not more than 1 wt. %, in particular not more than 0.1 wt. %, and especially not more than 0.01 wt. %.

According to a first preferred embodiment, the liquid phase is selected from water and aqueous solvents, i.e. solvent mixtures which in addition to water also contain up to 20 wt. %, preferably however not more than 10 wt. %, based on the total quantity of water and solvent, of one or more organic solvents miscible with water, for example ethers miscible with water such as tetrahydrofuran, methyl glycol, methyl diglycol, alkanols such as isopropanol or polyols such as glycol, glycerine, diethylene glycol, propylene glycol and the like. Such formulations are also referred to below as suspension concentrates (SCs).

Such suspension concentrates contain tembotrione as form A or as form C in a finely divided particulate form, wherein the particles of the form A or C are present suspended in an aqueous phase. The size of the active substance particles, i.e. the size which 90 wt. % of the active substance particles do not exceed, here typically lies below 30 μm, in particular below 20 μm. Advantageously, in the SCs according to the invention, at least 40 wt. % and in particular at least 60 wt. % of the particles have diameters below 2 μm.

In such SCs the quantity of active substance, i.e. the total quantity of tembotrione and of other active substances if necessary, usually lies in the range from 10 to 70 wt. %, in particular in the range from 20 to 50 wt. %, based on the total weight of the suspension concentrate.

In addition to the active substance, aqueous suspension concentrates typically contain surface-active substances, and also if necessary antifoaming agents, thickeners (=rheology modifiers), antifreeze agents, stabilizers (biocides), agents for adjusting the pH and anticaking agents.

Possible surface-active substances are the previously named surface-active substances. Preferably the aqueous plant protection agents according to the invention contain at least one of the previously named anionic surfactants and if necessary one or more nonionic surfactants, if necessary in combination with a protective colloid. The quantity of surface-active substances will as a rule be 1 to 50 wt. %, in particular 2 to 30 wt. %, based on the total weight of the aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Concerning the nature and quantity of the antifoaming agents, thickeners, antifreeze agents and biocides, the same applies as aforesaid.

If necessary, the aqueous SCs according to the invention can contain buffers for pH regulation. Examples of buffers are alkali metal salts of weak inorganic or organic acids, such as for example phosphoric acid, boric acid, acetic acid, propionic acid, citric acid, fumaric acid, tartaric acid, oxalic acid and succinic acid.

According to a second preferred embodiment, the liquid phase consists of non-aqueous organic solvents in which the solubility of the form A or C of tembotrione at 25° C. and 1013 mbar is not more than 1 wt. %, in particular not more than 0.1 wt. %, and especially not more than 0.01 wt. %. These include in particular aliphatic and cycloaliphatic hydrocarbons and oils, in particular those of plant origin, and also $C_1$-$C_4$ alkyl esters of saturated or unsaturated fatty acids or fatty acid mixtures, in particular the methyl esters, for example methyl oleate, methyl stearate and rape oil methyl ester, but also paraffinic mineral oils and the like. Accordingly, the present invention relates also to agents for plant protection in the form of a non-aqueous suspension concentrate, which will also be referred to below as OD (oil-dispersion). Such ODs contain the form A or form C of tembotrione in a finely divided particulate form, wherein the particles of the form A or C are present suspended in a non-aqueous phase. The size of the active substance particles, i.e. the size which 90 wt. % of the active substance particles do not exceed, here typically lies below 30 μm, in particular below 20 μm. Advantageously, in the non-aqueous suspension concentrates, at least 40 wt. % and in particular at least 60 wt. % of the particles have diameters below 2 μm.

In such ODs, the quantity of active substance, i.e. the total quantity of tembotrione and of other active substances if necessary, usually lies in the range from 10 to 70 wt. %, in particular in the range from 20 to 50 wt. %, based on the total weight of the non-aqueous suspension concentrate.

In addition to the active substance and the liquid carrier, non-aqueous suspension concentrates typically contain surface-active substances, and also if necessary antifoaming agents, agents to modify the rheology and stabilizers (biocides).

Possible surface-active substances are preferably the previously named anionic and nonionic surfactants. The quantity of surface-active substances will as a rule be 1 to 30 wt. %, in particular 2 to 20 wt. %, based on the total weight of the non-aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

The forms A and C of tembotrione according to the invention can also be formulated as solid plant protection agents. These include powder, scattering and dusting agents but also water-dispersible powders and granules, for example coated, impregnated and homogenous granules. Such formulations can be produced by mixing or simultaneous grinding of the forms A or C of tembotrione with a solid carrier and if necessary other additives, in particular surface-active substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder or other solid carriers. Solid formulations can also be produced by spray drying, if necessary in the presence of polymeric or inorganic drying aids, and if necessary in the presence of solid carriers. For the production of solid formulations of tembotrione of form A or C, extrusion processes, fluidized bed granulation, spray granulation and comparable technologies are suitable.

Possible surface-active substances are the previously named surfactants and protective colloids. The quantity of surface-active substances will as a rule be 1 to 30 wt. %, in particular 2 to 20 wt. %, based on the total weight of the solid formulation according to the invention.

In such solid formulations, the quantity of active substance, i.e. the total quantity of tembotrione and of other active substances if necessary, usually lies in the range from 10 to 70 wt. %, in particular in the range from 20 to 50 wt. %, based on the total weight of the solid formulation.

The following formulation examples illustrate the production of such preparations:

I. Water-Dispersible Powder:
20 parts by weight of form A or form C are mixed well with 3 parts by weight of the sodium salt of diisobutylnaphthalenesulfonic acid, 17 parts by weight of the sodium salt of a ligninsulfonic acid from a sulfite waste liquor and 60 parts by weight of powdered silica gel and ground in a hammer mill. In this manner, a water-dispersible powder which contains the form A or C is obtained.

II. Dusting Agent
5 parts by weight of the form A or form C are mixed with 95 parts by weight of finely divided kaolin. In this manner, a dusting agent which contains 5 wt. % of the form A or C is obtained.

III. Non-Aqueous Suspension Concentrate:
20 parts by weight of form A or form C are mixed intimately with 2 parts by weight of the calcium salt of dodecylbenzenesulfonic acid, 8 parts by weight of fatty alcohol polyglycol ether, 2 parts by weight of the sodium salt of a phenolsulfonic acid urea formaldehyde condensate and 68 parts by weight of a paraffinic mineral oil. A stable, non-aqueous suspension concentrate of the form A or C is obtained.

IV. Non-Aqueous Suspension Concentrate:
20 parts by weight of form A or form C are ground to a fine active substance suspension in an agitator ball mill with the addition of 10 parts by weight of dispersants and wetting agents and 70 parts by weight of a paraffinic mineral oil. A stable, non-aqueous suspension concentrate of the form A or C is obtained. On dilution in water, a stable suspension of the active substance is obtained. The active substance content in the formulation is 20 wt. %.

V. Aqueous Suspension Concentrate:
10 parts by weight of form A or form C are formulated as an aqueous suspension concentrate in a solution of 17 parts by weight of a poly(ethylene glycol)(propylene glycol) block copolymer, 2 parts by weight of a phenolsulfonic acid formaldehyde condensate and about 1 part by weight of other additives (thickeners, foam suppressants) in a mixture of 7 parts by weight of propylene glycol and 63 parts by weight of water.

VI. Aqueous Suspension Concentrate:
20 parts by weight of form A or form C are ground to a fine active substance suspension in a stirred ball mill with the addition of 10 parts by weight of dispersants and wetting agents and 70 parts by weight of water. On dilution in water, a stable suspension of the active substance is obtained. The active substance content in the formulation is 20 wt. %.

VII. Water-Dispersible and Water-Soluble Granules
50 parts by weight of form A or form C are finely ground with the addition of 50 parts by weight of dispersants and wetting agents and formulated as water-dispersible or water-soluble granules by means of industrial devices (for example extrusion, spray tower, fluidized bed). On dilution in water, a stable dispersion or solution of the active substance is obtained. The formulation has an active substance content of 50 wt. %.

VIII. Water-Dispersible and Water-Soluble Powder
75 parts by weight of form A or form B are ground in a rotor-stator mill with the addition of 25 parts by weight of dispersants and wetting agents and also silica gel. On dilution in water, a stable dispersion or solution of the active substance is obtained. The active substance content of the formulation is 75 wt. %.

IX. Gel Formulations:
20 parts by weight of form A or form C, 10 parts by weight of dispersant, 1 part by weight of gelling agent and 70 parts by weight of water or an organic solvent are ground to a fine suspension in a ball mill. On dilution in water, a stable suspension is obtained. The active substance content of the formulation is 20 wt. %.

X. Directly Usable Granules (GR, FG, GG, MG)
0.5 parts by weight of the form A or form C are finely ground and combined with 99.5 parts by weight of carriers. Common processes here are extrusion, spray drying or fluidized bed. Granules for direct application with 0.5 wt. % active substance content are thus obtained.

The application of the form A or form C or the herbicidal agents containing them is effected, if the formulation is not already ready for use, in the form of aqueous spray fluids. These are prepared by dilution of the aforesaid formulations containing the form A or form C with water. The spray fluids can also contain other components in dissolved, emulsified or suspended form, for example fertilizers, active substances of other herbicidal or growth-regulating active substance groups, other active substances, for example active substances for combating animal pests or phyto-pathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention.

The application of the form A or form C or of the plant protection agents containing them can be effected in a pre-emergence or in a post-emergence method. If tembotrione is less tolerable for certain crop plants, application techniques can be used wherein the herbicidal agents are sprayed using the spraying equipment in such a manner that the leaves of the sensitive crop plants are as far as possible not hit, while the active substances reach the leaves of undesired plants growing under them or the uncovered soil surface (post-directed, lay-by).

The quantities of tembotrione applied are 0.001 to 3.0 kg active substance per hectare, preferably 0.01 to 1.0 kg active substance (a.S)/ha, depending on the treatment aim, season, target plants and growth stage.

In a further embodiment, the application of the form A or form C or the plant protection agent containing them can be effected by treatment of seed.

Treatment of seed essentially includes all techniques with which the person skilled in the art is familiar (seed dressing, seed coating, seed dusting, seed soaking, seed film coating, seed multilayer coating, seed encrusting, seed dripping and seed pelleting) on the basis of tembotrione in form A or C, or agents prepared therefrom. Here the plant protection agents can be applied diluted or undiluted.

The term seed includes seed of all types, for example grains, seeds, fruits, tubers, cuttings and similar forms. Preferably, the term seed here describes grains and seeds.

As seed, seed of the crop plants mentioned above but also the seeds of transgenic plants or those obtained by conventional breeding methods can be used.

For the seed treatment, tembotrione is normally used in quantities of 0.001 to 10 kg per 100 kg of seed.

To broaden the spectrum of action and to achieve synergistic effects, the forms A or C can be mixed and applied together with many members of other herbicidal or growth regulating active substance groups. In addition, it can be advantageous to formulate or apply tembotrione together with safeners.

For example, 1,2,4-thiadiazoles, 1,3,4-thiadiazoles, amides, aminophosphoric acids and derivatives thereof, aminotriazoles, anilides, aryloxy-/heteroaryloxyalkanoic acids and derivatives thereof, benzoic acid and derivatives thereof, benzothiadiazinones, 2-(heteroyl-/aroyl)-1,3-cyclohexanediones, heteroaryl aryl ketones, benzylisoxazolidinones, meta-$CF_3$-phenyl derivatives, carbamates, quinolinecarboxylic acid and derivatives thereof, chloracetanilides, cyclohexanone oxime ether derivatives, diazines, dichloropropionic acid and derivatives thereof, dihydrobenzofurans, dihydrofuran-3-ones, dinitroanilines, dinitrophenols, diphenyl ethers, dipyridyls, halogen-carboxylic acids and derivatives thereof, ureas, 3-phenyluracils, imidazoles, imidazolinones, N-phenyl-3,4,5,6-tetra-hydrophthalimides, oxadiazoles, oxiranes, phenols, aryloxy- and heteroaryloxyphenoxypropionic acid esters, phenylacetic acid and derivatives thereof, 2-phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolecarboxamides, uracils and phenylpyrazolines and isoxazolines and derivatives thereof are possible mixing partners. Particularly suitable as mixing partners are coherbicides such as terbuthylazin, bromoxynil, the sodium salt thereof and esters thereof with $C_4$-$C_8$ carboxylic acids, dicamba, S-metolachlor or pethoxamid, and safeners such as isoxadifen.

In addition, it can be of value to apply the form A or C alone or in combination with other herbicides also mixed with still further plant protection agents, together for example with agents for combating pests or phytopathogenic fungi or bacteria. Also of interest is the miscibility with mineral salt solutions which are used for the elimination of nutritional and trace element deficiencies. Additives such as non-phytotoxic oils and oil concentrates can also be added.

The invention claimed is:
1. A crystalline form A of 2-[2-chloro-4-methyl-sulfonyl-3-(2,2,2-trifluoroethoxymethyebenzoyl]-cyclohexan-1,3-dione, which in an X-ray powder diffraction diagram at 25° C. and Cu—Kα radiation displays at least 3 of the following reflections, quoted as 2θ values: 5.6±0.2°, 8.9±0.2°, 11.1±0.2°, 14.0±0.2°, 18.9±0.2°, 23.4±0.2°, 26.7±0.2°, 28.9±0.2° and 36.2±0.2°.

2. The crystalline form A of claim 1 with a content of 2-[2-chloro-4-methylsulfonyl-3-(2,2,2-trifluoroethoxymethyl)benzoyl]cyclohexan-1,3-dione of at least 94 wt. %.

3. 2-[2-chloro-4-methylsulfonyl-3-(2,2,2-trifluoroethoxymethyl)benzoyl]cyclohexan-1,3-dione consisting of at least 90 wt. % of crystalline form A of claim 1.

4. A process for the production of the crystalline form A of claim 1, comprising:
   i) preparing a solution of 2-[2-chloro-4-methylsulfonyl-3-(2,2,2-trifluoro-ethoxymethyl)-benzoyl]cyclohexan-1,3-dione in a polar organic solvent which is selected from the group consisting of cyclic ethers, acetonitrile, methanol, nitromethane, acetic acid, methyl ethyl ketone, pyridine and dimethyl sulfoxide, and
   ii) effecting a crystallization of 2-[2-chloro-4-methylsulfonyl-3-(2,2,2-trifluoro-ethoxymethyl)-benzoyl]cyclohexan-1,3-dione
   thereby obtaining the crystalline form A of 2-[2-chloro-4-methylsulfonyl-3-(2,2,2-trifluoroethoxymethyl)-benzoyl]cyclohexan-1,3-dione.

5. A crystalline form C of 2-[2-chloro-4-methyl-sulfonyl-3-(2,2,2-trifluoroethoxymethyl)-benzoyl]-cyclohexan-1,3-dione, which in an X-ray powder diffraction diagram at 25° C. and Cu—Kα radiation displays at least 3 of the following reflections, quoted as 2θ values: 7.4±0.2°, 10.8±0.2°, 14.8±0.2°, 16.6±0.2°, 21.1±0.2°, 21.6±0.2° and 33.6±0.2°.

6. The crystalline form C of claim 5 with a content of 2-[2-chloro-4-methylsulfonyl-3-(2,2,2-trifluoroethoxymethyl)benzoyl]cyclohexan-1,3-dione of at least 94 wt. %.

7. 2-[2-chloro-4-methylsulfonyl-3-(2,2,2-trifluoroethoxymethyl)benzoyl]-cyclohexan-1,3-dione consisting of at least 90 wt. % of crystalline form C of claim 5.

8. A process for the production of the crystalline form C of claim 5 comprising:
   i) preparing a hot solution having a temperature of at least 80° C. of 2-[2-chloro-4-methylsulfonyl-3-(2,2,2-trifluoroethoxymethyl)-benzoyl]cyclohexan-1,3-dione in 2,2-dimethyl-propanol or in an aromatic hydrocarbon or in a mixture of an aromatic hydrocarbon with an aliphatic hydrocarbon, and
   ii) effecting a crystallization of 2-[2-chloro-4-methylsulfonyl-3-(2,2,2-trifluoroethoxymethyl)-benzoyl]cyclohexan-1,3-dione by cooling of the solution
   thereby obtaining the crystalline form C of 2-[2-chloro-4-methylsulfonyl-3-(2,2,2-trifluoroethoxymethyl)-benzoyl]cyclohexan-1,3-dione.

9. A plant protection agent containing 2-[2-chloro-4-methylsulfonyl-3-(2,2,2-trifluoroethoxymethyl)-benzoyl]cyclohexan-1,3-dione which consists of at least 90 wt. % of the crystalline form A of claim 1, and one or more additives customary for the formulation of plant protection agents.

10. The plant protection agent of claim 9 in the form of an aqueous suspension concentrate.

11. The plant protection agent of claim 9 in the form of a non-aqueous suspension concentrate.

12. The plant protection agent of claim 9 in the form of a powder or granules dispersible in water.

13. A plant protection agent containing 2-[2-chloro-4-methylsulfonyl-3-(2,2,2-trifluoroethoxymethyl)-benzoyl]cyclohexan-1,3-dione which consists of at least 90 wt. % of the crystalline form C of claim 5 and one or more additives customary for the formulation of plant protection agents.

14. The plant protection agent of claim 13 in the form of an aqueous suspension concentrate.

15. The plant protection agent of claim 13 in the form of a non-aqueous suspension concentrate.

16. The plant protection agent of claim 13 in the form of a powder or granules dispersible in water.

17. A method for combating undesired plant growth, wherein 2-[2-chloro-4-methylsulfonyl-3-(2,2,2-trifluoroethoxymethyl)-benzoyl]cyclohexan-1,3-dione consisting of at least 90 wt. % of the crystalline form A of claim 1 is used on plants, the habitat thereof and/or on seeds.

18. A method for combating undesired plant growth, wherein 2-[2-chloro-4-methylsulfonyl-3-(2,2,2-trifluoroethoxymethyl)-benzoyl]cyclohexan-1,3-dione consisting of at least 90 wt. % of the crystalline form C of claim 5 is used on plants, the habitat thereof and/or on seeds.

* * * * *

UNITED STATES PATENT AND TRADEMARK OFFICE
CERTIFICATE OF CORRECTION

PATENT NO.        : 8,309,769 B2
APPLICATION NO.   : 12/530666
DATED             : November 13, 2012
INVENTOR(S)       : Eike Hupe et al.

Page 1 of 1

It is certified that error appears in the above-identified patent and that said Letters Patent is hereby corrected as shown below:

On the cover page, item (54) and col. 1, line 1, the title of the application should be:

--Crystalline forms of 2-[2-chloro-4-methylsulfonyl-3-(2,2,2-trifluoroethoxymethyl)benzoyl] cyclohexan-1,3-dione--; and Claim 1, col. 21, line 61-63, delete
"2-[2-chloro-4-methyl-sulfonyl-3-(2,2,2-trifluoroethoxymethyebenzoyl]-cyclohexan-1,3-dione", and insert --2-[2-chloro-4-methyl-sulfonyl-3-(2,2,2-trifluoroethoxymethyl)benzoyl]-cyclohexan-1,3-dione--.

Signed and Sealed this
Twelfth Day of February, 2013

Teresa Stanek Rea
*Acting Director of the United States Patent and Trademark Office*